(12) United States Patent
Neer

(10) Patent No.: US 8,133,198 B2
(45) Date of Patent: Mar. 13, 2012

(54) MEDICAL FLUID INJECTOR HAVING A THERMO-MECHANICAL DRIVE

(75) Inventor: Charles S. Neer, Cincinnati, OH (US)

(73) Assignee: Mallinckrodt LLC, Hazelwood, MO (US)

( * ) Notice: Subject to any disclaimer, the term of this patent is extended or adjusted under 35 U.S.C. 154(b) by 194 days.

(21) Appl. No.: 12/439,212

(22) PCT Filed: Oct. 24, 2007

(86) PCT No.: PCT/US2007/022565
§ 371 (c)(1), (2), (4) Date: Feb. 27, 2009

(87) PCT Pub. No.: WO2008/057223
PCT Pub. Date: May 15, 2008

(65) Prior Publication Data
US 2010/0004534 A1 Jan. 7, 2010

Related U.S. Application Data

(60) Provisional application No. 60/854,529, filed on Oct. 26, 2006.

(51) Int. Cl.
*A61M 37/00* (2006.01)
(52) U.S. Cl. .......................................... 604/90; 604/131
(58) Field of Classification Search ............... 604/90, 604/70, 131, 113, 291
See application file for complete search history.

(56) References Cited

U.S. PATENT DOCUMENTS

| | | | |
|---|---|---|---|
| 4,070,859 A * | 1/1978 | Sobecks | 60/530 |
| 4,121,425 A * | 10/1978 | Nicodemus | 60/670 |
| 4,861,340 A | 8/1989 | Smith et al. | |
| 4,944,726 A | 7/1990 | Hilal et al. | |
| 5,062,834 A | 11/1991 | Gross et al. | |
| 5,197,322 A | 3/1993 | Indravudh | |
| 5,505,706 A | 4/1996 | Maus et al. | |
| 5,571,261 A | 11/1996 | Sancoff et al. | |
| 2002/0156418 A1 | 10/2002 | Gonnelli et al. | |
| 2004/0115068 A1 | 6/2004 | Hansen et al. | |
| 2008/0287873 A1 * | 11/2008 | Liberatore et al. | 604/131 |

FOREIGN PATENT DOCUMENTS

| | | |
|---|---|---|
| EP | 0385916 | 9/1990 |
| EP | 1 570 875 | 9/2005 |
| EP | 0 232 164 | 8/2007 |
| WO | WO 01/72357 | 10/2001 |

* cited by examiner

*Primary Examiner* — Kevin C Sirmons
*Assistant Examiner* — Deanna K Hall
(74) *Attorney, Agent, or Firm* — Marsh Fischmann & Breyfogle LLP

(57) ABSTRACT

A medical fluid injector and methods for operation thereof. In certain embodiments, the medical fluid injector includes a medium that is expandable and contractible in response to a thermal gradient, a thermal device coupled to the medium, and a syringe interface coupled to the medium. The thermal device may include a heater, a cooler, or a combination thereof.

24 Claims, 7 Drawing Sheets

MEDICAL FLUID INJECTOR HAVING A THERMO-MECHANICAL DRIVE

CROSS-REFERENCE TO RELATED APPLICATIONS

This patent application is a U.S. National Stage of PCT/US2007/022565, filed on Oct. 24, 2007, which claims priority to U.S. Provisional Patent Application Ser. No. 60/854,529, filed on Oct. 26, 2006. Priority is claimed to each patent application set forth in this Related Applications section. the invention as defined by the following appended claims.

FIELD OF THE INVENTION

The invention relates generally to drives for powered medical fluid injectors and, more specifically, to a thermo-mechanical drive for such an injector.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Powered injectors are typically utilized to administer a volume of medical fluid, such as a contrast agent, into a patient before and/or while the patient is examined with imaging equipment. Generally, an electric motor in the powered injector is utilized to move a plunger of a syringe through the syringe, and the medical fluid is injected into the patient due the movement of the plunger. Frequently, the patient is examined with an imaging device (e.g., an MRI system), and detected contrast agent in the patient is utilized by the imaging device in generating image data.

Unfortunately, many powered injectors are incompatible with certain types of imaging equipment. For example, electric motors used to drive powered injectors often include magnets and/or ferrous materials that can interfere with operation of an MRI machine. For instance, due to the presence of magnets and/or ferrous material in the injector, the injector may be drawn toward and/or pulled into the MRI machine, thus causing potential risk of injury to the patient and/or damage to the injector and/or MRI machine. As another example, electromagnetic fields from the injector's electric motor may be picked up by the MRI machine and cause undesired artifacts in the resulting images produced by the MRI machine.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

In certain aspects, the present invention generally relates to a substantially non-ferrous drive for a powered medical fluid injector. Certain subsequently discussed embodiments include a thermo-mechanical drive that heats or cools a substance to actuate a syringe. In some embodiments, the temperature of the substance may be changed (e.g., increased) to expand the substance and drive a plunger through the syringe to expel medical fluid from the syringe. In some embodiments, the temperature of the substance may be changed (e.g., decreased) to contract the substance and withdraw the plunger (e.g., to pull medical fluid into the syringe for a subsequent injection procedure). Some embodiments of the injector may be devoid of electric motors to drive the syringe and, thus, facilitate use of the injector near MRI machines.

A first aspect of the present invention is directed to a medical fluid injector that includes a medium that is expandable and contractible in response to a thermal gradient. The injector also includes a thermal device (e.g., a heater, a cooler, or a combination thereof) that is in thermal communication with the medium. Incidentally, one thing is "in thermal communication" with another thing if heat energy can be directly and/or indirectly transferred therebetween. In addition to the thermal device, the injector also includes a syringe interface that is coupled to the medium.

A second aspect of the invention is directed to a drive for a medical fluid injector. The drive includes a fluid disposed in a reservoir, a thermal device in thermal communication with the fluid, an actuator in fluid communication with the reservoir, and a syringe interface coupled to the actuator.

Yet a third aspect of the invention is directed to a method of operation for a medical fluid injector. In this method, the heat energy of a material is changed. This change in heat energy at least temporarily causes an alteration in volume of the material. In other words, this change in heat energy causes the volume of the material to increase or decrease. This alteration in the volume of the material causes a plunger of a syringe to move (e.g., to draw fluid into or expel fluid out of the syringe).

Various refinements exist of the features noted above in relation to the various aspects of the present invention. Further features may also be incorporated in these various aspects as well. These refinements and additional features may exist individually or in any combination. For instance, various features discussed below in relation to one or more of the illustrated embodiments may be incorporated into any of the above-described aspects of the present invention alone or in any combination. Again, the brief summary presented above is intended only to familiarize the reader with certain aspects and contexts of the present invention without limitation to the claimed subject matter.

BRIEF DESCRIPTION OF THE FIGURES

Various features, aspects, and advantages of the present invention will become better understood when the following detailed description is read with reference to the accompanying figures in which like characters represent like parts throughout the figures, wherein.

DETAILED DESCRIPTION OF SPECIFIC EMBODIMENTS

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a", "an", "the", and "said" are intended to mean that there are one or more of the elements. The terms "comprising", "including", and "having" are intended to be inclusive and mean that there may be additional elements other than the listed elements. Moreover, the use of "top", "bottom", "above", "below" and variations of these terms is made for convenience, but does not require any particular orientation of the components. As used herein, the term "coupled" refers to the condition of being directly or indirectly connected or in contact. Additionally, the phrase "in fluid communication" indicates that fluid and/or fluid pressure may be transmitted from one object to another.

Figure 1:
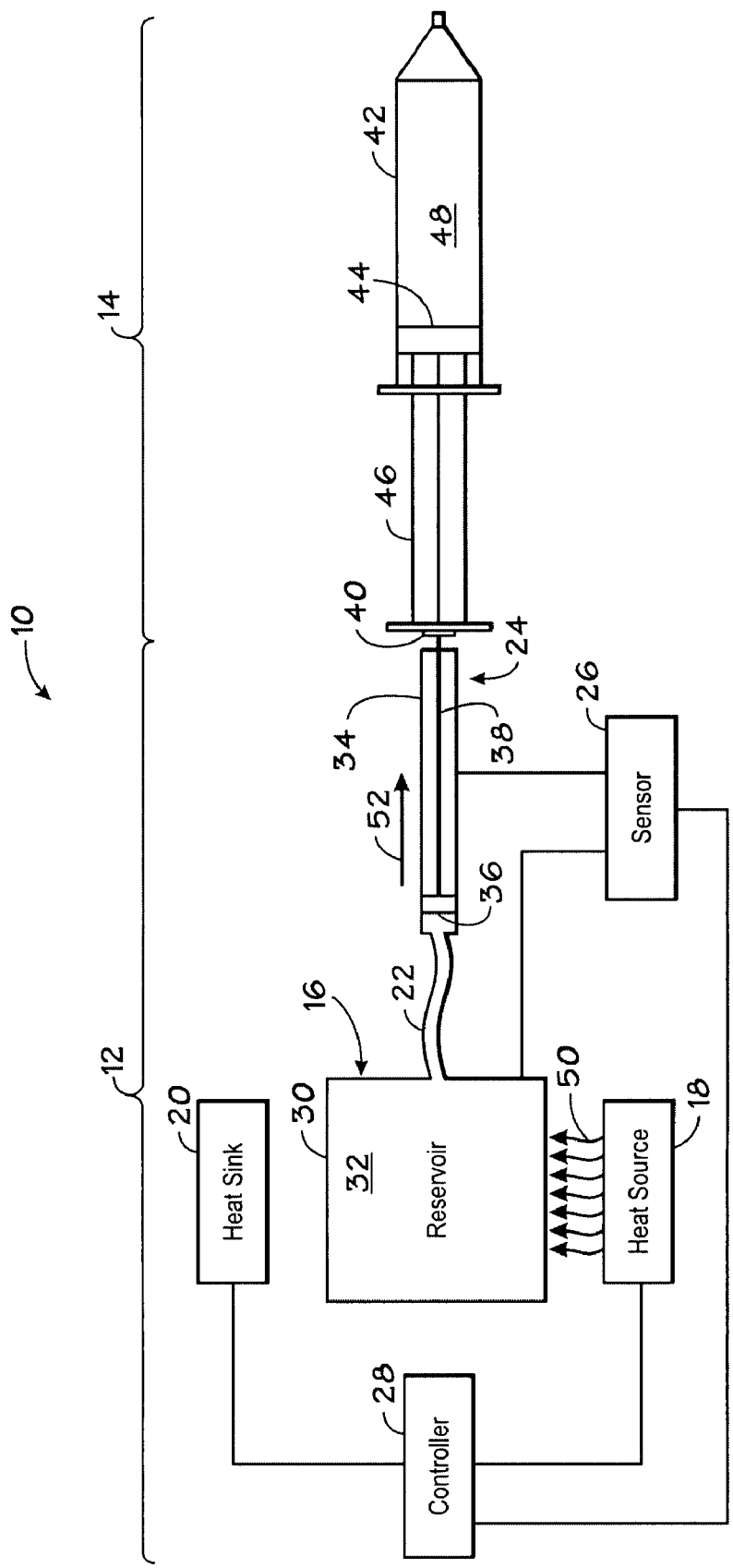
FIG. 1 is a diagram of a medical fluid injector beginning to inject a medical fluid.

FIG. 1 depicts an exemplary injection system 10, which includes a medical fluid injector 12 and a syringe 14. The injector 12 includes a substance and is designed to heat and/or cool the substance (e.g., liquid) to cause a resulting change in volume of the substance, thus causing actuation of the syringe 14. The injection system 10 may be substantially or entirely non-ferrous. To this end, the system 10 may include very little, if any, parts (e.g., electric motors) having ferrous material that might interfere with operation of an MRI machine.

The injector 12 includes a reservoir 16, a heat source 18, a heat sink 20, a fluid conduit 22, an actuator 24, a sensor 26, and a controller 28, details of which are described below. The combination of the heat source 18 and the heat sink 20 is one example of what may be referred to herein as a thermal device. Some embodiments of the injector 12 may include a fluid thermo-mechanical actuator that operates as a thermal gradient and causes a fluid (e.g., liquid and/or gas) thereof to expand and/or contract to induce movement. Other embodiments of the injector 12 may include a solid thermo-mechanical actuator that operates as a thermal gradient and causes a solid to expand and/or contract to induce movement.

The reservoir 16 of the injector 12 has walls 30 that may be made of any appropriate material. For instance, the walls 30 may consist essentially of non-ferrous material exhibiting a high thermal conductivity, such as aluminum, stainless steel, copper, or a combination thereof. To enhance heat transfer through the walls 30, the walls 30 may include structures that increase surface area, such as fins, rods, undulations and/or texturing. These structures may be on the inside and/or outside surfaces of the reservoir 16. The walls 30 preferably define a structure that is substantially rigid and substantially non-deformable with respect to forces arising from pressure differentials across the walls 30. The reservoir 16 may exhibit any appropriate design/configuration. For instance, the reservoir 16 may have a rectangular cross-sectional shape, circular cross sectional shape, square cross-sectional shape, or other cross-sectional shape.

The reservoir 16 contains a fluid 32 (e.g., a liquid). The fluid 32 may be substantially incompressible, have a phase change temperature outside of a range of temperatures to which the fluid 32 is exposed during operation of the injector, and/or have a large coefficient of thermal expansion, e.g., the coefficient of thermal expansion may be greater than $1 * 10^{-3}$ $C.^{-1}$. The fluid 32 may include water, alcohol, oil, mercury, or a combination thereof. In some embodiments, the fluid 32 may have a liquid-to-gas phase change temperature at or near a temperature of the environment in which the powered injector 12 is operated (e.g., near room temperature).

The heat source 18 is in thermal communication with the fluid 32. Herein, two bodies are said to be "in thermal communication" if heat energy may flow from one body to the other. The heat source 18 may include or refer to any appropriate heat source such as a resistive heater (e.g., a coil of wire), an inductive heater, a heat pipe, a Peltier device, a heat pump, a radiant heater, a microwave source, and/or a room providing ambient heat. The heat source 18 may be disposed outside the reservoir 16, inside the reservoir 16, or both outside and inside the reservoir 16. In certain embodiments, the heat source 18 may be configured to convert electrical energy into heat energy and heat the fluid 32 in the reservoir 16.

The injector 12 of FIG. 1 also includes a heat sink 20. The heat sink 20 may include or refer to any appropriate heat sink such as a Peltier device, a refrigeration system, a heat pipe, and/or a surrounding room to absorb heat. As with the heat source 18, the heat sink 20 may be disposed inside, outside, or both inside and outside of the reservoir 30.

In some embodiments, the heat sink 20 and heat source 18 may be integrated into a single device. For example, a thermoelectric device, such as a Peltier device, may heat or cool depending on whether the device is forward or reverse biased. In another example, a heat pump may operate as both a refrigeration system and a heater.

A fluid conduit 22 may connect to the reservoir 16. The fluid conduit 22, in some embodiments, may be the only outlet for fluid 32 from the reservoir 16. The fluid conduit 22 may include appropriate fittings to connect to the reservoir 16. In some embodiments, the fluid conduit 22 includes substantially non-expandable tubing, such as a hydraulic line. The fluid conduit 22 is illustrated as housing at least a portion of the fluid 32 and being connected to the actuator 24 of the injector 12.

The actuator 24 of the injector 12 is shown as having a barrel 34, a piston head 36, a rod 38, and a syringe interface 40. The barrel 34 may be a generally cylindrical tube with substantially rigid walls. In some embodiments, the piston head 36 may be described as a fluidly movable member (i.e., a member that moves in response to a difference in fluid pressure). The barrel 34 and the piston head 36 may be cylindrical, polygonal, or any other suitable geometry. In certain embodiments, the barrel 34 may have a diameter of about 0.4 inch (e.g., 0.375 inch) and a length of about 5.0 inches. The piston head 36 may fit within the barrel 34, and it may be shaped and sized to form a moveable seal against the walls of the barrel 34. Fluid 32 may occupy the space inside the barrel 34 on one side of the piston head 36. The rod 38 may extend from the piston head 36 on the side of the piston head 36 opposite the fluid 32. The syringe interface 40 may be disposed at the distal end of the rod 38. The syringe interface 40 may include a plate or surface to press against a syringe 14 or an interlocking member or device to couple to a syringe 14, for instance.

One or more sensors 26 may be positioned to sense a variety of parameters, such as the position of the piston head 36 in the barrel 34, the pressure of the fluid 32, and/or the temperature of the fluid 32. For instance, a linear position transducer may be attached to both a reference point (e.g., the barrel 34) and a moving part (e.g., the piston head 36, the rod 38, or the syringe interface 40). Alternatively, or additionally, parameters of the fluid 32 may be monitored by a thermocouple or pressure transducer.

The controller 28 of the present embodiment may include circuitry and/or code configured to modulate the position of the syringe interface 40 by signaling the heat source 18 and/or heat sink 20 to add or remove heat from the fluid 32. In some embodiments, the controller 28 may include feedback circuitry or code adapted to control the position of the syringe interface 40, the rate of movement of the syringe interface 40, and/or the magnitude of force applied by the syringe interface 40. Alternatively, or additionally, the controller 28 may have circuitry and/or code adapted to control the temperature of the fluid 32, the rate of change of the temperature of the fluid 32, the pressure of the fluid 32, and/or the rate of change of the pressure of the fluid 32. The circuitry and/or code may be configured to exercise in situ or ex situ feedback or feed forward control of one or more of these parameters.

A variety of devices may embody all or part of the controller 28, such as a microprocessor, a computer, a personal computer, micro-controller, an application specific integrated circuit, a digital signal processor, and/or a central processing unit. The controller 28 may include various forms of tangible machine readable memory, such as dynamic random access memory, flash memory, static random access memory, a hard disc drive, an optical drive, and/or a magnetic tape drive. In some embodiments, the memory may store code configured to control the powered injector 12. The controller 28 may also include devices to interface with the sensor 26, the heat source 18, and the heat sink 20, such as an analog-to-digital converter, an amplifier circuit, and/or a driver circuit. While the controller 28 is depicted in FIG. 1 as a single block, it should be understood that, in some embodiments, the controller 28 may include a variety of components remotely disposed from one another. Thus, while some embodiments may include an integrated or monolithic controller 28, FIG. 1 should be regarded as depicting a logical or functional unit rather than as depicting a single device.

Turning to the syringe 14, the illustrated syringe 14 may include a barrel 42, a plunger 44, and a push rod 46. The barrel 42 may be made of glass or plastic and have a generally cylindrical tubular shape. The plunger 44 may be shaped to fit within the barrel 42 and slidably seal against the walls of the barrel 42. Together, the illustrated barrel 42 and plunger 44 may house a medical fluid 48, such as a liquid pharmaceutical, a liquid contrast agent, or saline, for example. The push rod 46 may extend from a side of the plunger 44 opposite the medical fluid 48 and interface with syringe interface 40 of the actuator 24. In some embodiments, the barrel 42 of the syringe 14 may be secured in fixed relation to the barrel 34 of the actuator 24 by, for instance, a chassis or frame. The syringe 14 may be in fluid communication with a patient or organism via tubing and a hypodermic needle.

Figure 2:
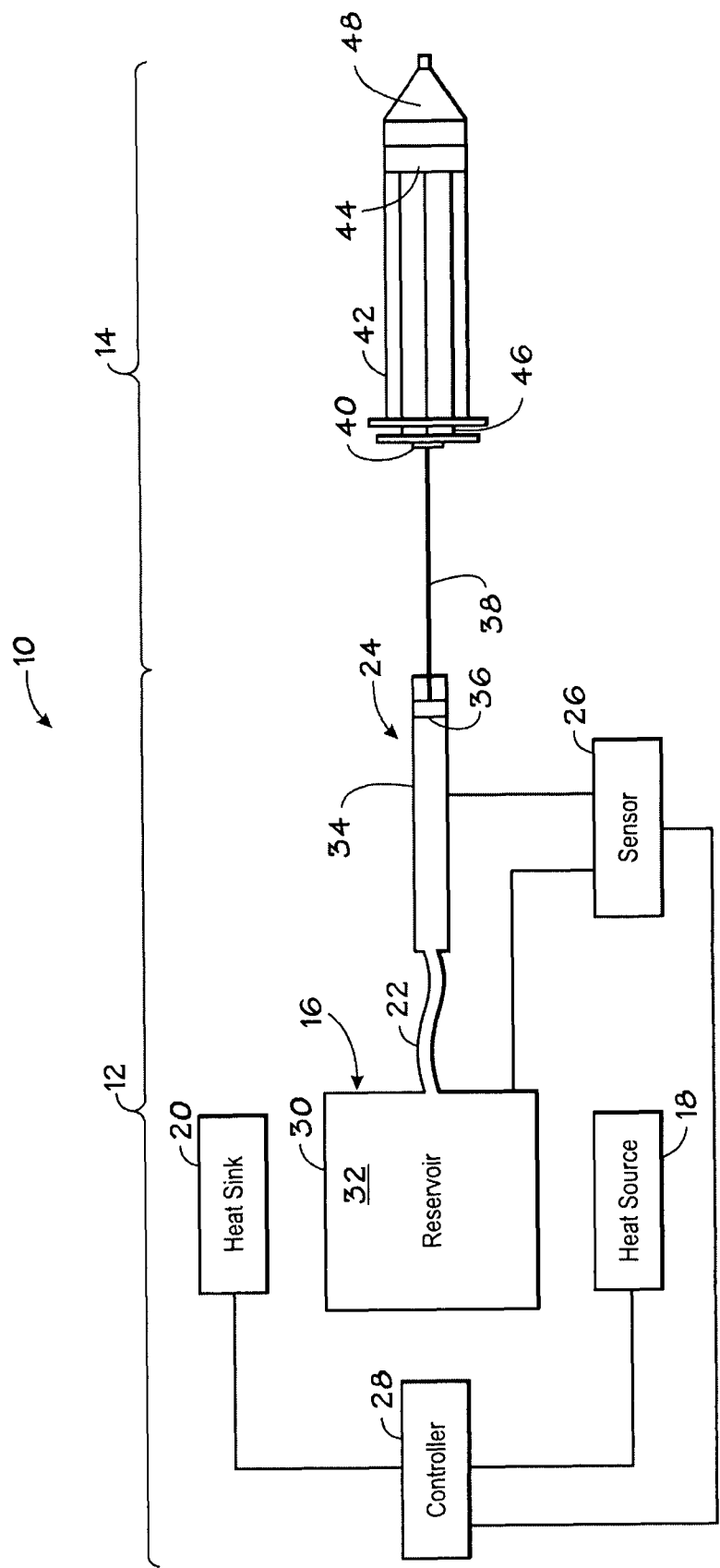
FIG. 2 is a diagram of the injector of FIG. 1 after injecting the fluid.

In operation, the injection system 10 may pump the medical fluid 48 into a patient, as depicted by FIGS. 1, 2. Specifically, FIG. 1 depicts the initiation of an injection, and FIG. 2 illustrates the injection system 10 at or near the end of an injection. To initiate an injection, user may signal the controller 28 to begin injecting by pressing a button, turning a dial, or otherwise indicating a desire to begin injecting the medical fluid 48. In response, the controller 28 may signal the heat source 18 to apply heat energy 50 to the fluid 32. The heat source 18, in turn, may generate a thermal gradient between the fluid 32 and the heat source 18, with the heat source 18 at a higher temperature. For example, the controller 28 may signal the heat source 18 by closing an electric current path to a resistive heater disposed in or near the fluid 32. As the fluid 32 is heated, it may expand due to thermal expansion. In some embodiments, the fluid 32 may expand without changing phase, e.g., the fluid 32 may remain a liquid during injection.

As the fluid 32 expands, it may cause the syringe interface 40 to move, as indicated by arrow 52. The expanding fluid 32 may build pressure within the reservoir 16. Some of the expanding fluid 32 may flow through the fluid conduit 22 and into the actuator 24. The pressurized fluid 32 may apply a force to the piston head 36 in the direction of arrow 52. This force may drive the piston head 36 through the barrel 34. The piston head 36, in turn, may drive the rod 38, which may push the syringe interface 40. As the syringe interface 40 moves in the direction of arrow 52, it may push the plunger 44 through the barrel 42 of the syringe 14 via the push rod 46. In the present embodiment, the plunger 44 may drive the medical fluid 48 out of the syringe 14 and into a patient or other organism.

During injection, the controller 28 may exercise feedback or feed forward control over a variety of parameters. For example, the controller 28 may receive feedback signals from the sensor 26 indicative of the fluid 32 temperature, the fluid 32 pressure, the position of the syringe interface 40, the velocity of the interface 40, the flow rate, and/or the rate of change of one or more of these parameters. In some embodiments, the controller 28 may output a signal to the heat source 18 in response to one or more of these feedback signals. For instance, the controller 28 may control the volume of medical fluid 48 injected, the rate at which the medical fluid 48 is injected, the distance that the syringe interface 40 travels, the speed of the syringe interface 40, the temperature of fluid 32, the rate of change of the temperature of fluid 32, the volume of fluid 32, the rate of change of the volume of fluid 32, the pressure of fluid 32, and/or the rate of change of pressure of fluid 32. The controller 28 may target a set point for one or more of these parameters. In some embodiments, the set point or controlled parameter may vary during injection according to a profile (e.g., velocity profile or flow rate profile) stored in memory. For example, the syringe interface 40 may move at a first speed for the first 10 seconds of an injection and a second, different speed, for the remainder of the injection.

As illustrated by FIG. 2, near the end of the presently discussed injection, the piston head 36 may have traveled through the barrel 34 of the actuator 24, and the plunger 44 may have traveled through the barrel 42 of the syringe 14. At this point, the syringe 14 may have pumped a portion of the medical fluid 48 into the patient via a hypodermic needle or other device. At or near the end of an injection, the controller 28 may signal the heat source 18 to stop adding heat 50 to the fluid 32, reduce the amount of heat added to the fluid 32, or apply heat 50 to the fluid 32 at a rate that maintains the temperature of the fluid 32. The controller 28 may also output a signal indicating that the injection is complete to an audio or visual indicator, such as a speaker, light emitting diode, a liquid crystal display, a cathode ray tube, an organic light emitting diode display, or the like.

Figure 3:
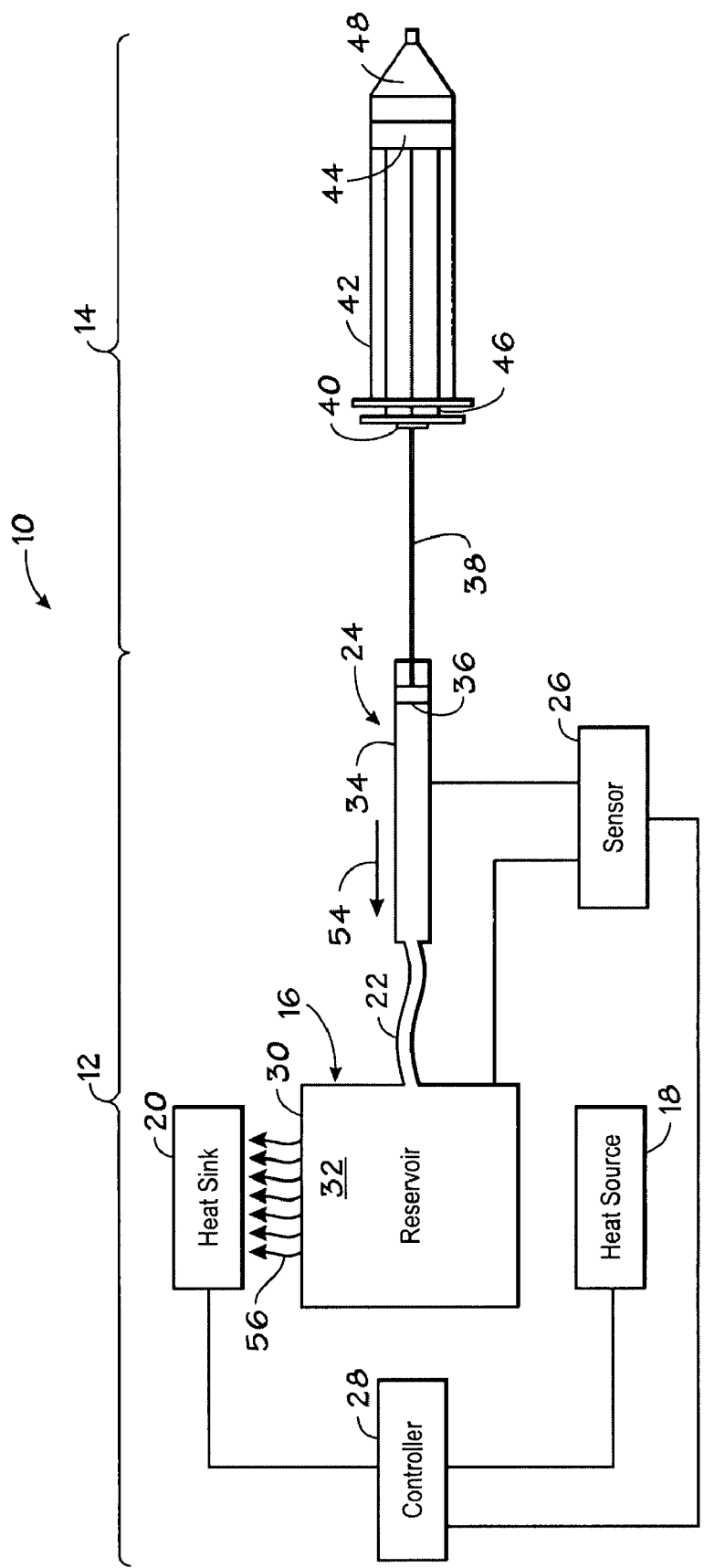
FIG. 3 is a diagram of the injector of FIG. 1 loading a syringe.

FIG. 3 depicts the powered injector 12 as the syringe 14 is reset or loaded. In the present embodiment, the powered injector 12 may pull the syringe interface backward, as indicated by arrow 54. The movement indicated by arrow 54 may be initiated by a user signaling a desire to reset the powered injector or load the syringe 14 through a user interface. The controller 28 may receive this signal and, in response, signal the heat sink 20 to cool the fluid 32 in the reservoir 16. The heat sink 20, in turn, may form a thermal gradient between the heat sink 20 and the fluid 32, and heat energy 56 may flow from the fluid 32 to the heat sink 20. For example, the controller 28 may close a current path to a Peltier cooler, and the Peltier cooler may accept heat from the fluid 32.

As thermal energy is removed from the fluid 32, the fluid 32 may contract and apply a negative pressure (i.e., a negative gauge pressure) to the piston head 36. In other words, by removing thermal energy from the fluid 32, a negative change in the volume of the fluid 32 may be induced, and the change in volume may pull the piston head 36. The piston head 36 may draw back through the barrel 36 in the direction of arrow 54. In some embodiments, the syringe interface 40 may be coupled to the push rod 46, and the syringe 14 may be loaded as the piston head 36 is drawn toward the reservoir 16. In alternative embodiments, the fluid conduit 22 may couple to the barrel 34 or the opposite side of the piston head 36, such that cooling causes the movement 52 and heating causes the movement 54.

Figure 4:
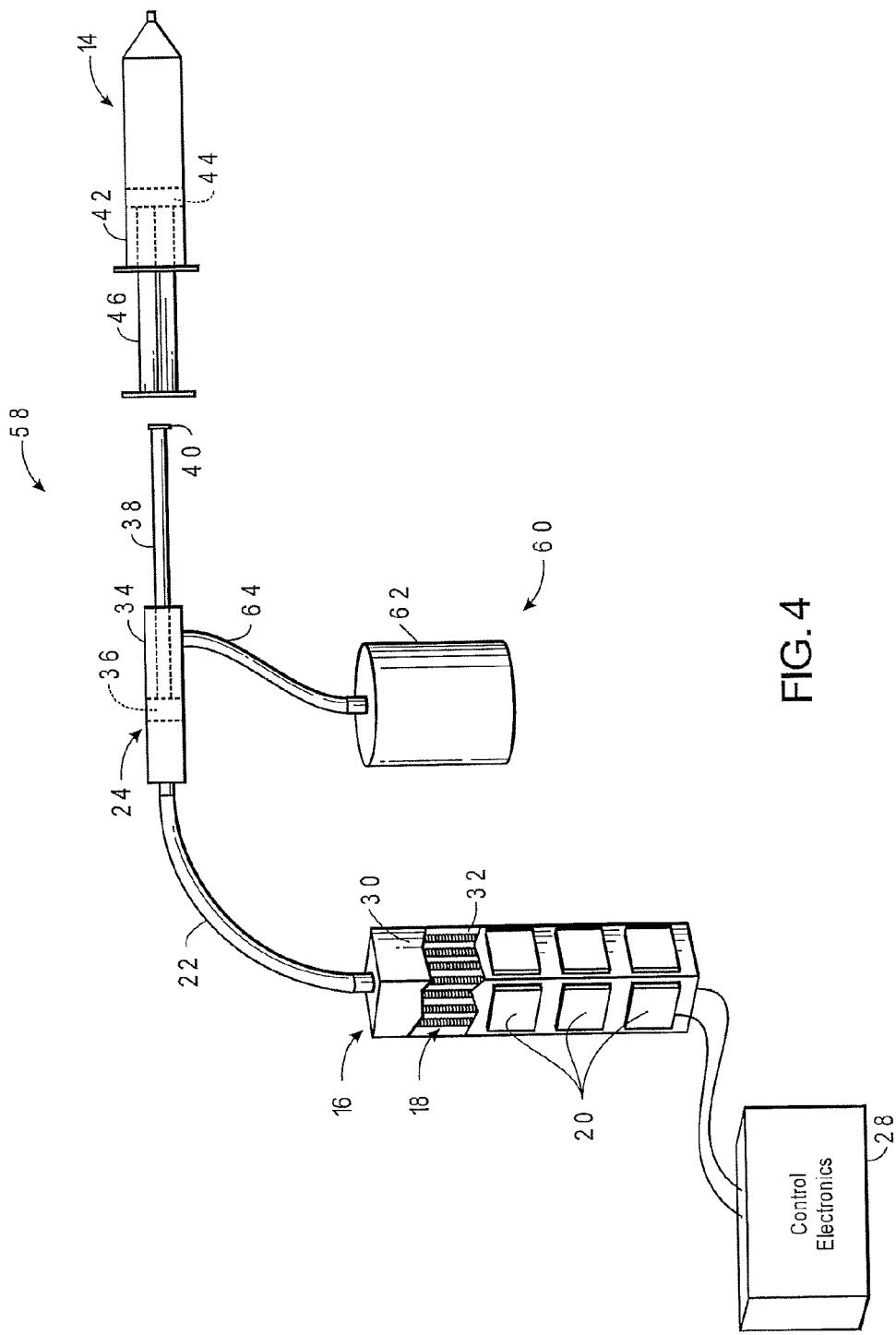
FIG. 4 is a perspective view of another medical fluid injector.

FIG. 4 depicts another exemplary injection system 58. In this embodiment, the heat source 18 includes an array of resistive heating coils disposed within the reservoir 16, and the heat sink 20 includes an array of Peltier coolers disposed on the exterior surface of the reservoir 16. The present embodiment also includes a reset air assist assembly 60 having a pressure vessel 62 and a gas conduit 64. The gas conduit 64 fluidically couples the pressure vessel 62 to the barrel 34 of the actuator 24. Specifically, in the present embodiment, the gas conduit 64 connects to a portion of the barrel 34 that is on an opposite side of the piston head 36 relative to the fluid conduit 22. Thus, in the current embodiment, pressure from the pressure vessel 62 counteracts pressure from the fluid 32.

In operation, the piston head 36 may pressurize the pressure vessel 62 as the piston head 36 is extended. Then, during loading of the syringe 14, or resetting of the injection system 58, the pressure from the pressure vessel 62 may drive the piston head 36 into a retracted position in the barrel 34. In some embodiments, the pressure vessel may contain air or other appropriate compressible gas.

Figure 5:
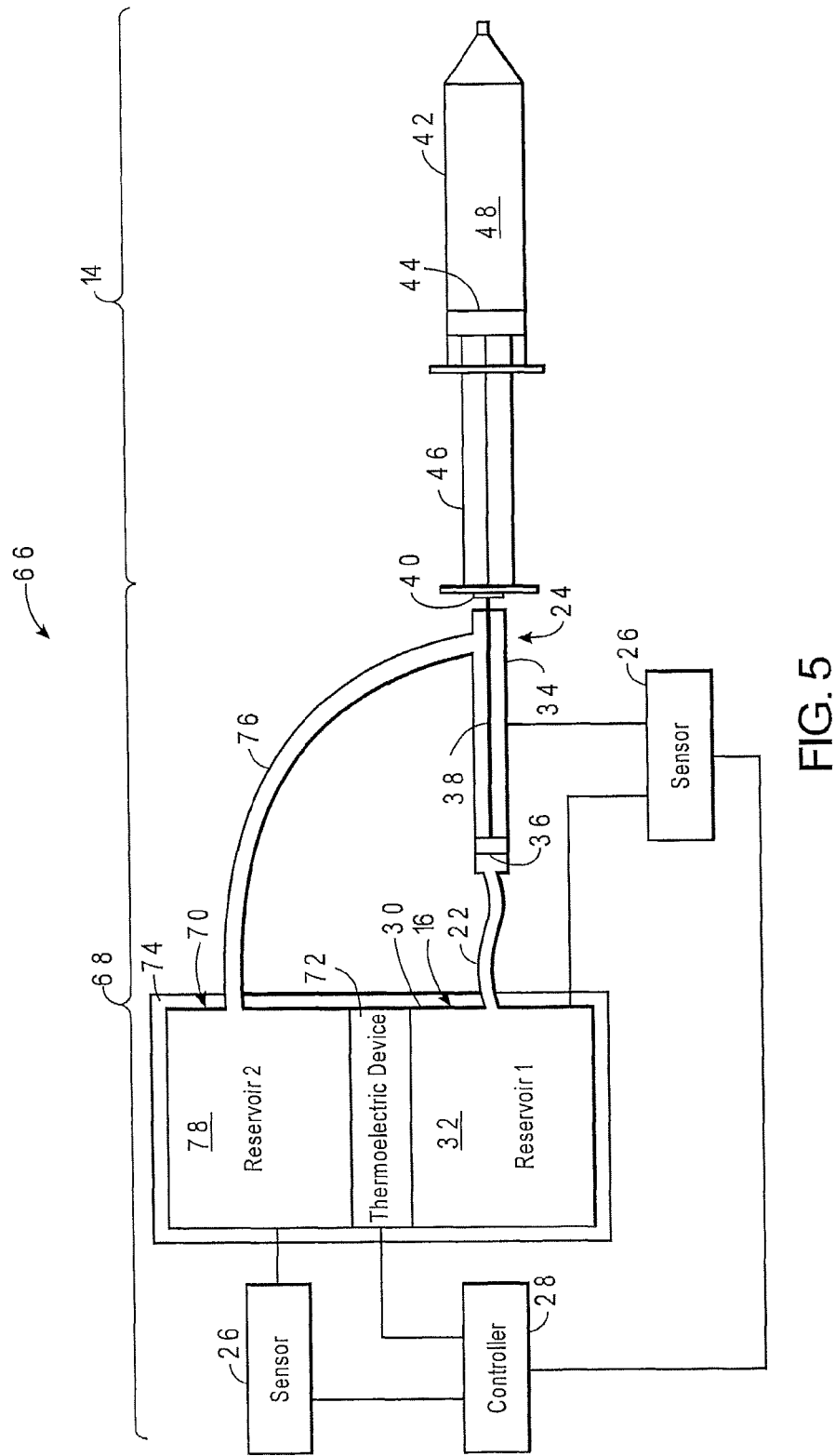
FIG. 5 is a diagram of a dual-temperature injector.

FIG. 5 illustrates another exemplary injection system 66. The present embodiment includes a dual-temperature injector 68 that may have dual reservoirs 16, 70, a reversible thermoelectric device 72, insulation 74, a second fluid conduit 76, and a second body of fluid 78. The thermoelectric device 72 may include a Peltier-Seebeck device adapted to transfer heat energy from one reservoir 16, 70 to the other reservoir 16, 70 in response to a current. Further, the direction in which the thermoelectric device 72 transfers heat may depend on the direction in which current powering the thermoelectric device 72 flows. That is, current flow in a first direction may result in heat being transferred from the first reservoir 16 to the second reservoir 70, and current flow in an opposite direction may result in heat being transferred from the second reservoir 70 to the first reservoir 16.

As assembled, the thermoelectric device 72 may be disposed between and in thermal communication with the reservoirs 16, 70. In some embodiments, the insulation 74 may envelope the reservoirs 16, 70 and the thermoelectric device 72. The second fluid conduit 76 may fluidically couple the second reservoir 70 to the actuator 24. More specifically, the second fluid conduit 76 may couple to the volume of the barrel 34 opposite the piston head 36 from the fluid 32.

In operation, the controller 28 may initiate injection by signaling the thermoelectric device 72 to transfer heat from the second reservoir 70 to the first reservoir 16. For instance, the controller 28 may drive a current through the thermoelectric device 70 in a first direction. As discussed above, application of heat energy to the first reservoir 16 may result in the fluid 32 expanding and driving the piston head 36 forward. At the same time, removal of heat energy from the second reservoir 70 may cause the volume of fluid 78 to decrease, thereby tending to pull the piston head 36 forward. In other words, in the present embodiment, fluid 32 pushes the piston head 36 while fluid 78 pulls it during injection.

To retract the piston head 36, the controller 28 may reverse the direction of the current applied to the thermoelectric device 72. In response, the thermoelectric device 72 may reverse the direction in which it transfers heat, and heat energy may flow from the first reservoir 16 to the second reservoir 70. As the first reservoir 16 cools, and the second reservoir 70 warms, the fluid 78 may push the piston head 36 back through the barrel 34, and the fluid 32 may pull the piston head 36 in the same direction.

Figure 6:
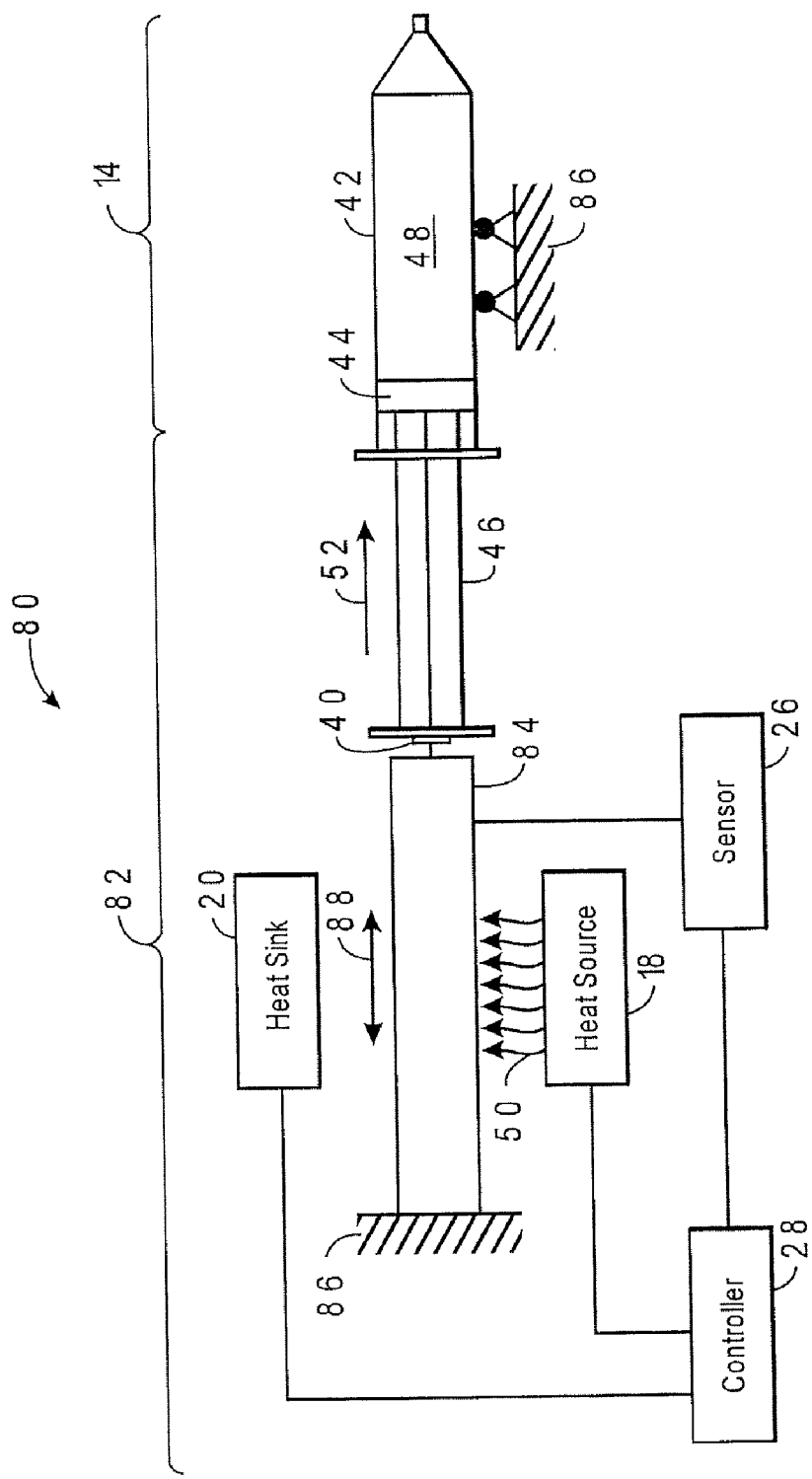
FIG. 6 is a diagram of an injector having a solid thermo-mechanical actuator.

FIG. 6 is another exemplary injection system 80. The present embodiment may include a powered injector 82 having a solid thermo-mechanical actuator 84. The solid thermo-mechanical actuator 84 may include shape memory alloys, shape memory polymers, or other materials with a high thermal coefficient of expansion. In some embodiments, the actuator 84 may be substantially or entirely non-ferrous. The actuator 84 and syringe 14 may be secured to a chassis 86 that holds them in fixed relation.

In operation, the heat source 18 may deliver heat energy 50 to the actuator 84, and the actuator 84 may expand. In some embodiments, a current is conducted through the actuator 84, and internal resistive heating generates heat energy 50. As the actuator 84 is heated, it may expand, as illustrated by arrow 88. At the same time, the syringe interface 40 may drive the plunger 44 through the barrel 42 of the syringe 14, as depicted by arrow 52. After injection, the heat sink 20 may retract the actuator 84 by removing heat energy from the actuator 82.

Figure 7:
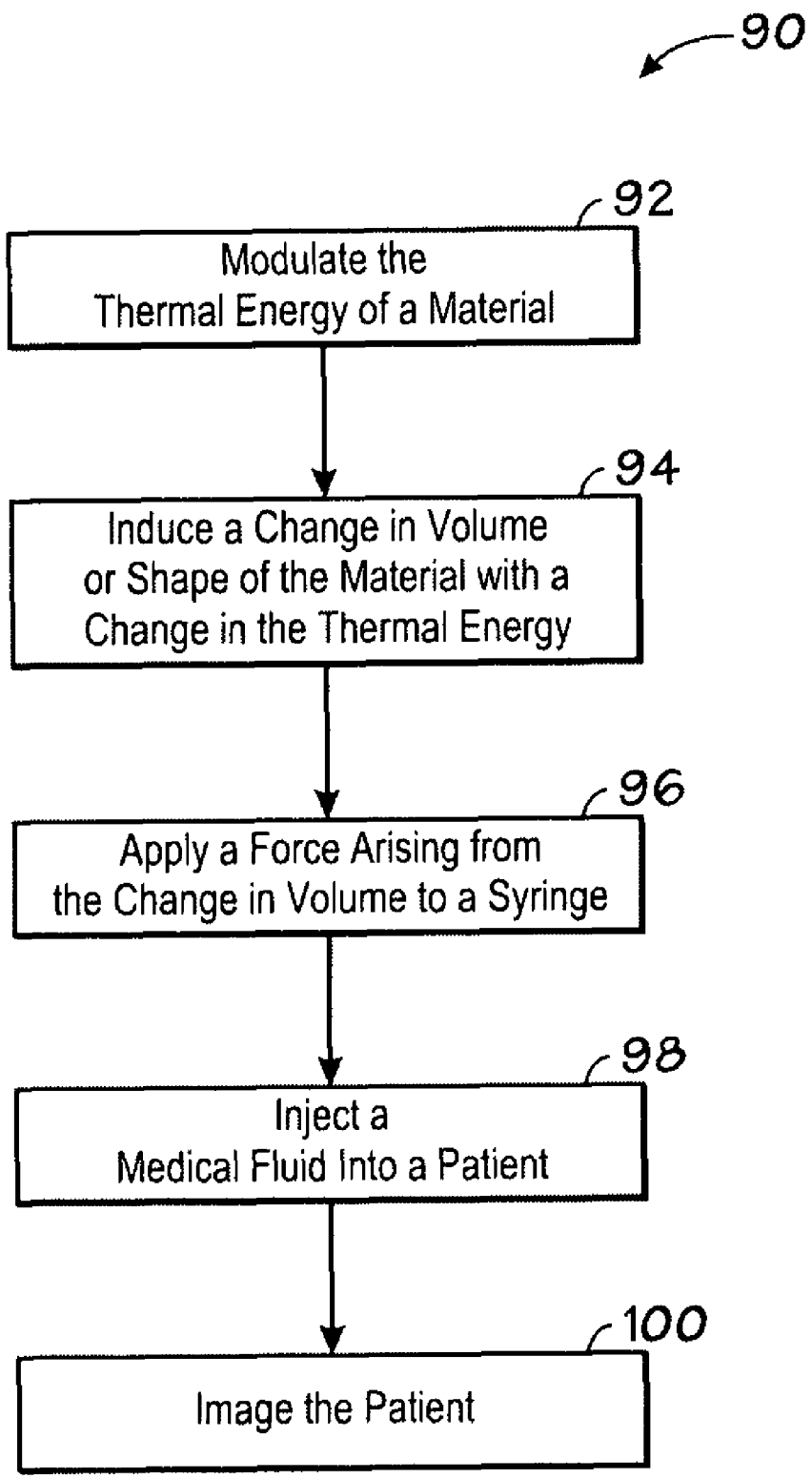
FIG. 7 is a flow chart depicting an exemplary injection process.

FIG. 7 is a flow chart depicting an exemplary injection process 90, which may be performed by one or more of the previously discussed embodiments. The process 90 begins with modulating the thermal energy of a material, as depicted by block 92. Modulating the thermal energy may include transferring heat energy by conduction, convection, radiation, resistive heating, chemical heating, mechanically heating, or a combination thereof. In some embodiments, modulating the thermal energy may include raising or lowering the temperature of the material.

Next, or at substantially the same time, a change in the volume or shape of the material is induced by the resulting change in thermal energy, as depicted by block 94, and a force arising from the change in volume is applied to a syringe, as depicted block 96. As the material translates to the new volume or shape, in the present embodiment, a medical fluid is injected into a patient by the syringe, as depicted by block 98.

Finally, the patient is imaged, as depicted by block 100. Imaging the patient may be performed with a variety of types of imaging systems, such as a projection radiography system (e.g., an x-ray system), a fluoroscopy system, a tomography system (e.g., a computed axial tomography system), a magnetic resonance imaging (MRI) system, and/or an ultrasound system, for instance. Certain non-ferrous embodiments may tend to minimize interference with MRI systems.

While the invention may be susceptible to various modifications and alternative forms, specific embodiments have been shown by way of example in the figures and have been described in detail herein. However, it should be understood that the invention is not intended to be limited to the particular forms disclosed. Rather, the invention is to cover all modifications, equivalents, and alternatives falling within the spirit and scope of

The invention claimed is:

1. A medical fluid injector, the injector comprising:
   a medium that is expandable and contractible in response to a thermal gradient;
   a thermal device in thermal communication with the medium, wherein the thermal device comprises a heater and a cooler;
   a controller in communication with each of the heater and the cooler; and
   a syringe interface coupled to the medium, wherein the syringe interface is movable by the medium, wherein the controller signals the heater to move the syringe interface in a first direction, and wherein the controller signals the cooler to move the syringe interface in a second direction.

2. The injector of claim 1, wherein the medium is a solid.

3. The injector of claim 1, wherein the medium is a fluid.

4. The injector of claim 3, wherein the fluid comprises a substantially incompressible liquid that is disposed within a generally closed system, and wherein the syringe interface is coupled to a fluidly movable member within the generally closed system.

5. The injector of claim 4, wherein the substantially incompressible liquid comprises alcohol.

6. The injector of claim 1, further comprising:
   a fluid thermo-mechanical actuator that comprises a pressure vessel, a conduit coupled to the pressure vessel, a barrel coupled to the conduit, and a piston disposed movably in the barrel, and wherein the syringe interface is coupled to the piston, and wherein each of the heater and cooler is in thermal communication with the pressure vessel.

7. The injector of claim 1, wherein the medium comprises first and second mediums isolated from one another, and wherein the thermal device is disposed between the first and second mediums.

8. The injector of claim 7, wherein the first and second mediums comprise first and second fluids disposed in first and second chambers, and wherein the first and second chambers are fluidly coupled to opposite sides of a piston coupled to the syringe interface.

9. The injector of claim 1, wherein the thermal device comprises a thermoelectric device.

10. The injector of claim 1, further comprising:
    a syringe in contact with the syringe interface.

11. The injector of claim 1, further comprising:
    a sensor.

12. The injector of claim 11, wherein the controller interacts with the sensor.

13. The injector of claim 12, wherein the controller receives at least one feedback signal from the sensor indicative of at least one of a temperature of the medium, a pressure of the medium, a position of the syringe interface, a velocity of the syringe interface, and a flow rate associated with a movement of the syringe interface.

14. The injector of claim 10, wherein the syringe comprises a barrel and a plunger disposed within and movable relative to the barrel, wherein the controller signals the thermal device to move the syringe interface in the first direction which in turn moves the plunger in one direction, and wherein the controller signals the thermal device to move the syringe interface in the second direction which in turn moves the plunger in another direction.

15. The injector of claim 14, wherein the first direction is associated with a discharge of medical fluid from the syringe, and wherein the second direction is associated with a loading of medical fluid into the syringe.

16. The injector of claim 14, wherein the syringe interface is coupled with a push rod of the syringe, and wherein the push rod extends from the plunger of the syringe and interfaces with the syringe interface.

17. The injector of claim 1, wherein the medium comprises first and second fluids within first and second reservoirs, respectively, wherein the thermal device is in thermal communication with each of the first and second reservoirs, wherein the injector further comprises an actuator, wherein the actuator comprises a piston, a barrel, and the syringe interface, wherein a movable seal exists between the piston and the barrel, wherein the piston is coupled to the syringe interface, wherein the first reservoir is fluidly connected with a first side of the piston, wherein the second reservoir is fluidly connected to a second side of the piston, and wherein the first and second sides of the piston are fluidly isolated from each other by the seal between the piston and the barrel.

18. The injector of claim 17, wherein a first operation of the thermal device transfers heat between the first and second reservoirs such that the first medium pushes on the piston head and the second medium pulls on the piston head to move the piston head in the first direction, and wherein a second operation of the thermal device transfers heat between the first and second reservoirs such that the first medium pulls on the piston head and the second medium pushes on the piston head to move the piston head in the second direction that is opposite of the first direction.

19. A method of operation for a medical fluid injector, the method comprising:
    interacting a first fluid with a first side of a piston; and
    moving the piston in each of first and second axial directions solely by fluid pressure acting directly on the piston, wherein the moving comprises:
        expanding the first fluid to move the piston in the first axial direction, wherein the expanding of the first fluid comprises heating the first fluid;
        advancing a plunger of a syringe in one direction in response to movement of the piston resulting from the expanding of the first fluid;
        contracting the first fluid to move the piston in the second axial direction, wherein the contracting of the first fluid comprises cooling the first fluid; and
        advancing the plunger of the syringe in another direction in response to movement of the piston resulting from the contracting of the first fluid.

20. The method of claim 19, wherein fluid pressure provided by each of the expanding and contracting of the first fluid acts on the first side of the piston.

21. The method of claim 20, wherein the moving further comprises directing air from a pressure vessel against a second side of the piston during each of the expanding and contracting of the first fluid.

22. The method of claim 20, further comprising:
    interacting a second fluid with a second side of the piston that is opposite of the first side, wherein the moving further comprises:
        contracting the second fluid during the expanding of the first fluid, wherein the contracting of the second fluid comprises cooling the second fluid; and expanding the second fluid during the contracting of the first fluid, wherein the expanding of the second fluid comprises heating the second fluid.

23. The method of claim 19, wherein the advancing of the plunger of the syringe in the one direction comprises expelling a contrast agent from the syringe.

24. The method of claim 19, wherein the advancing of the plunger of the syringe in the one direction comprises expelling a radiopharmaceutical from the syringe.

* * * * *